United States Patent [19]

Mercer

[11] Patent Number: 5,102,902

[45] Date of Patent: Apr. 7, 1992

[54] REAGENTS AND METHOD FOR THERAPEUTIC TREATMENT OF MULTIPLE SCLEROSIS

[76] Inventor: James B. Mercer, 13109 W. 95th St., Lenexa, Kans. 66215

[21] Appl. No.: 517,082

[22] Filed: May 1, 1990

Related U.S. Application Data

[63] Continuation of Ser. No. 206,651, Jun. 14, 1988, Pat. No. 4,952,594, which is a continuation-in-part of Ser. No. 720,021, Apr. 19, 1985, Pat. No. 4,871,759, which is a continuation-in-part of Ser. No. 407,808, Aug. 13, 1982, Pat. No. 4,537,775, which is a continuation-in-part of Ser. No. 64,072, Aug. 6, 1979, Pat. No. 4,346,095, which is a continuation-in-part of Ser. No. 876,618, Feb. 10, 1978, Pat. No. 4,177,281, which is a continuation-in-part of Ser. No. 656,336, Feb. 9, 1976, Pat. No. 4,073,928, which is a continuation-in-part of Ser. No. 514,798, Oct. 15, 1974, Pat. No. 3,952,103, which is a continuation-in-part of Ser. No. 370,952, Jun. 18, 1973, Pat. No. 3,856,966.

[51] Int. Cl.$^5$ ............................................. A61K 31/415
[52] U.S. Cl. ..................................................... 514/400
[58] Field of Search ............................................ 514/400

*Primary Examiner*—Jerome D. Goldberg
*Attorney, Agent, or Firm*—Litman, McMahon & Brown

[57] ABSTRACT

The administration internally to humans of certain imidazol derivatives, especially N''-cyano-N-methyl-N'-[2[[(5-methyl-1H-imidazol-4-yl) methyl]thio]-ethyl]-guanidine (cimetidine) or salts thereof, is an effective therapeutic treatment for multiple sclerosis, both acute and chronic. The imidazole moiety is theorized to directly inhibit spread of the virus theorized to cause multiple sclerosis. Treatment of multiple sclerosis with metronidazole with one bolus dose on a frequency of once a day or less and with cimetidine on a frequency of twice per day has been found to be highly efficatious with minimal suppression of the patient's natural immune system and minimal long term peripheral nerve damage.

6 Claims, No Drawings

REAGENTS AND METHOD FOR THERAPEUTIC TREATMENT OF MULTIPLE SCLEROSIS

This is a Continuation of U.S. application Ser. No. 206,651, filed June 14, 1988, entitled REAGENTS AND METHOD FOR THERAPEUTIC TREATMENT OF MULTIPLE SCLEROSIS, now U.S. Pat. No. 4,952,594 which was a Continuation-in-Part of U.S. application Ser. No. 720,021 filed Apr. 19, 1985, entitled METHOD OF TREATMENT OF MESENTERIC ADENITIS, now U.S. Pat. No. 4,871,759, which was a Continuation-in-Part of U.S. application Ser. No. 407,808 filed Aug. 13, 1982 entitled THERAPEUTIC TREATMENT FOR VIRAL INFECTIONS, now U.S. Pat. No. 4,537,775, which was a Continuation-in-Part of application Ser. No. 064,072, filed Aug. 6, 1979, now U.S. Pat. No. 4,346,095; which was a Continuation-in-Part of Ser. No. 876,618, filed Feb. 10, 1978, now Pat. No. 4,177,281; which was a Continuation-in-Part of Ser. No. 656,336, filed Feb. 9, 1976, now U.S. Pat. No. 4,073,928 which was a Continuation-in-Part of Ser. No. 514,798, filed Oct. 15, 1974, now U.S. Pat. No. 3,952,103; which was a Continuation-in-Part of Ser. No. 370,952, filed June 18, 1973, now U.S. Pat. No. 3,856,966.

BACKGROUND OF THE INVENTION

The invention herein described relates to an agent for, and a method of, treating progressive, nonremitting multiple sclerosis (hereinafter referred to as "multiple sclerosis"). In particular, this invention relates to the use of imidazole derivatives as general anti-viral agents.

Infectious agents, possibly viral in nature, together with an immune disorder, appear to cause multiple sclerosis. The following articles discuss theories relating to multiple sclerosis resulting from an infection, especially viral: Kurtzke, J. F., Hyllestad, K., *Multiple Sclerosis in the Faron Islands* Ann. Neurol 1979, Vol. 5, pages 6–21; Kurtzke, J. F., Gudmundson, K. R., Bergmann, S., *Multiple Sclerosis in Iceland:* 1. *Evidence of a Postwar Epidemic* Nour. 1982 Vol. 32, pages 143–50; Rosati, G., et al., *Incidence of Multiple Sclerosis in Macomber, Sardinia,* 1912–1981: *Onset of the Disease After* 1950, 14 Neurology 36, Jan. 1986.

Although it is not the intent of applicant to be bound herein to any particular theory or theories it is theorized by applicant and others that measles virus is the cause of multiple sclerosis. The following articles discuss this theory: Levy, N. L., Auerbach, P. S., Hayes, E. C., *A Blood Test for Multiple Sclerosis Based on the Adherence of Lymphocytes to Measles--Infected Cells,* N. Engl. J. Med. 294: 1424–27, 1976; Stevenson, J. R., Ter Meulen, V., Kisseling, W., *Search for Canine-Distemper Virus Antibodies in Multiple Sclerosis. A Detailed Variological Evaluation,* Lancet 2:772–75, 1980.

The measles virus genome appears to attack the susceptible gene of that particular chromosome that controls the production of myelin in central nervous system. This theory is discussed in Popko, B., Puckett, C., Lai, L., et al, *Myelin Deficient Mice: Expression of Myelin Basic Protein and Generation of Mice With Varying Levels of Myelin,* CEL 48:713–721, 1987.

In the past, treatments associated with multiple sclerosis have been ineffective for at least two reasons. There is substantial evidence that multiple sclerosis is virally caused and the significance of such evidence has not been recognized by the medical authorities. Thus, to date, no cure exists for multiple sclerosis because antiviral agents have not been thought of as an appropriate drug for this virally induced disease. In addition, when more commonly used drugs with anti-viral properties, such as cyclophosphamide, are used to treat non-virally related symptoms or secondary, non-viral infections, their anti-viral efficacy in patients with viral infections has been masked by secondary complications which usually arise because of the drug's toxicity. Accordingly, there is disagreement concerning the value of cyclophosphamide in view of the harmful side effects. See, for example *Cyclophosphamide, Should It be Used Daily, Monthly, or Never?* New Engl. J. of Med., Vol. 310 No. 7, Feb. 16, 1984. There are, however, effective anti-viral agents with much lower levels of toxicity which would also be an effective treatment for multiple sclerosis as a virally induced disease.

While multiple sclerosis has been treated with medication, treatment has often been directed solely toward symptoms or secondary infections rather than to the viral cause. In general the medication has not been selective to the infecting virus and goes on to produce serious or even deadly secondary complications, especially suppression of the immune system. With the immune system depressed other infections and cancer eventually invade the patient and cause greater sickness or death.

Many of the imidazole derivative drugs described herein have been previously used in medicine for various purposes; however, their potential as broad anti-viral agents has not been generally recognized, apparently because each derivative typically has uses not directly related to any anti-viral activity. Thus, with the exception of 1-(Beta-hydroxyethyl)-2-methyl-5-nitro-imidazole (metronidazole), none of the substances described herein have been previously characterized as anti-viral agents. Metronidazole was so characterized by the present applicant in his U.S. Pat. No. 4,346,095.

The recognition of a general anti-viral agent began with metronidazole. Metronidazole is a known alkylating agent and derivative of imidazole. It appears that metronidazole can penetrate nearly all tissues of the body quite readily. Initially, it was erroneously believed that metronidazole was highly toxic and carcinogenic. This false belief delayed the recognition of metronidazole as a valuable anti-viral agent. Much of this error was probably due to the improper interpretation of certain medical data concerning the substance. It appears there were two basic sources of the false conclusions concerning metronidazole.

The first false conclusion was that metronidazole causes birth defects in children when given in the first trimester of pregnancy for the treatment of venereal trichomoniasis. While the literature does include several unsupported allegations concerning such a use of metronidazole, one study shows that, when metronidazole is given in all trimesters of pregnancy, the fetus in utero is actually protected from infectious agents. It is these infectious agents that are believed to cause many major and minor birth defects in the developing fetus; therefore, there may be fewer birth defects under metronidazole therapy. See, e.g., Morgan, I.F.K. "Metronidazole Treatment in Pregnancy", *Int. J. Obst. & Gyn.*, Vol. 15, p. 501 (1978). In the Morgan study, the untreated control group of pregnant women actually had more still births and congenital fetal malformations than the metronidazole treated mothers. Also, there has never been any epidemiologic evidence to support a conclusion that metronidazole causes birth defects in humans or rodents.

The second false conclusion was that metronidazole was carcinogenic. This allegation derived from studies on Swiss mice. See Rustia, M., Shibik, P. *Experimental Induction of Hepatomas, Mammary Tumors and Other Tumors With Metronidazole in Noninbred Sas: WRC (WI) BR Rats,* JNCI, Vol. 63, p. 863 (1979) and *Induction of Lung . . . Lymphomas in Mice by Metronidazole;* JNCI, Vol. 48, p. 721 (1972). Rustia and Shubik were the principal proponents of the conclusion that metronidazole is carcinogenic. However, they apparently made several errors in arriving at this conclusion. First, they used unsuitable subjects, i.e. cancer-prone inbred animals. Second, they failed to recognize that the metronidazole fed Swiss mice significantly out-lived the controls. Since the metronidazole-fed rats outlived the controls and had fewer other diseases, a higher proportion of the metronidazole-fed animals would be expected to eventually develop cancer because they lived longer.

Applicant theorizes that the metronidazole prolonged the life of the subject species by suppressing viral infections until the immune system of the metronidazole-fed subject became depleted due to old age and could no longer prevent the natural onset of cancer or other diseases resulting from the failure of the immune system. Applicant specifically theorizes that the metronidazole was acting as an anti-viral agent and was controlling viral infection in the test subjects. With these viral infections controlled, the test species lived longer. Thus, metronidazole cannot be concluded as carcinogenic on the basis of this data.

Tests were conducted using metronidazole on humans for the treatment of viral related disorders. The metronidazole proved to be very beneficial in relieving such disorders. Details of these trials are discussed in the parent applications which are incorporated herein by reference and by the detailed description of the present application.

Metronidazole is a substituted imidazole of the formula $C_6H_9N_3O_3$. It has the following structure:

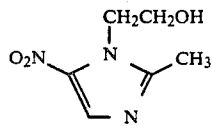

Metronidazole is theorized to interfere with nucleic acid biosynthesis and it is further theorized that its effectiveness in the treatment of viral infections relates to blockage or interference with the viral metabolism cycle necessary for cell infection. It appears likely that metronidazole acts by suppressing viral production while natural body defenses function to eliminate viral material from the system, although it is not the intent of applicant to be confined to this theory or, as noted before, the other theories presented herein.

Applicant has studied other compounds possessing a similar structure, the appropriate bioavailability and suitable non-fatal toxicological and carcinogenic properties as useful anti-viral agents. Applicant theoretically determined that the imidazole moiety of metronidazole was the active part of the compound. Therefore, it is postulated that other imidozole compounds, including N"-cyano-N-methyl-N'-[2[[(5-methyl-1H-imidazol-4-yl) methyl]thio]-ethyl]-guanidine (cimetidine), 6-[1-methyl-4-nitro-imidazol-5-yl) thio] purine (azathioprine) and L-(—)-2,3,5,6-Tetrahydro-6-phenyl-imidazo [2,1-b] thiazole (levamisole), would also be broad antiviral agents. In many instances the acid salt of the compound would be the actual drug administered; however, no distinction will be made between the substance and its salts herein.

Cimetidine is one of the most widely used drugs in the world. Its primary use has been in the treatment of gastritis, since it apparently markedly reduces the volume and concentration of acid secreted, both in the resting state and after stimulation by food, histamine, pentagestrin, insulin and caffeine. Despite its wide use in certain areas of medicine, cimetidine is not recognized as a nearly universal anti-viral agent.

In 1977, Van Der Spuy, Levy and Levin treated a woman having a gastric ulcer with cimetidine. The woman was also suffering from Herpes zoster at the time and under the cimetidine treatment she appeared to obtain relief from the herpetic pain. This led to a postulation that cimetidine might be useful in the treatment of herpes zoster infections. Further studies tended to support this hypothesis. For example see S. Van Der Spuy, D. W. Levy, W. Levin, *Cimetidine in the Treatment of Herpes Virus Infections,* SA Mediese Tydskrif, p. 112, 19 July 1980. However, while cimetidine was postulated by Levy et al. as a possible agent for treatment of herpes zoster, it was not recognized as a potentially universal, or nearly universal, anti-viral agent.

In addition, cimetidine may be too toxic for use in human immunal deficiency virus infected patients due to a tendency to cause blood dyscrasias.

Cimetidine has the formula $C_{10}H_{16}N_6S$ and exhibits the following chemical structure:

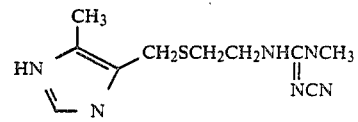

Thus, it is a substituted imidazole.

Applicant theorizes that, especially with metronidazole, fewer side effects, such as peripheral nerve damage sometimes associated with frequent doses of metronidazole, will result, if given in large infrequent doses (daily or less often) rather than in smaller multiple daily dosages. Single daily oral bolus doses give an effective lytic metronidazole dose and avoids the complicating peripheral neuropathy syndrome in patients with good kidneys.

Further, applicant theorizes that metronidazole is substantially less harmful than the other two imidazole derivatives (cimetidine and azathioprine) and is also substantially less harmful than cyclophosphormide, the anti-viral and chemotherapeutic agent in use for more than thirty years. The other three agents, unlike metronidazole, while effective in combating virus infections, also cause substantial damage to the immune system.

OBJECTS OF THE INVENTION

The objects of this invention are: to provide a class of substances for systematically treating multiple sclerosis; to provide a method of treating multiple sclerosis with these substances; to provide such a method that is suitable for intensive therapy as well as long-term maintenance and intermittent therapy; to provide such a method including the application of bolus doses of the substances at periods of one day or more to avoid complications; and to provide such a treatment which is easily administered with few or no complications and which is also usually well tolerated by the recipient.

Other objects and advantages of this invention will become apparent from the following descriptions and examples wherein are set forth, by way of illustration and example, certain embodiments of this invention.

SUMMARY OF THE INVENTION

Anti-viral agents are provided for treatment of viral and viral-related disorders, especially multiple sclerosis. These agents belong to a group of compounds which are derivatives of imidazole. It is theorized that the imidazole moeity acts directly to inhibit spread of a virus theorized to be the cause or theorized to combine with other unknown factors to be the cause of multiple sclerosis.

While it is believed that any non-toxic, pharmaceutically acceptable substituted imidazole of sufficient bioavailability may be administered according to the present invention, this application is especially directed to N"-cyano-N-methyl-N'-[2[[(5-methyl-1H-imidazol-4-yl) methyl]thio]-ethyl]-guanidine (cimetidine); (and salts thereof.

It is theorized that multiple sclerosis is caused by a measles virus present in genetically susceptible patients. For such patients, it is further theorized that the measles virus causing multiple sclerosis may be inherited. In genetically susceptible patients, a health immune system continuously attacks and maintains the presence of the virus in the hosts at such low levels that the virus is effectively dormant. It is only when the immune system of such patients is sufficiently compromised that the measles virus reproduce at a rate that exceeds the compromised immune system's ability to effectively respond. Under such circumstances, the virus appears to become activated and the symptoms of multiple sclerosis are manifested in the patient. The immune system, in genetically susceptible patients, can be compromised for any number of reasons, including other incidental virally induced diseases, extreme emotional or physical stress, and in female patients, from the immune system responses to pregnancy.

The administration of effective anti-viral amounts of pharmaceutically acceptable compositions comprising a substituted imidazole operates to compensate for the compromised and debilitated immune system by operating to kill the virus responsible for multiple sclerosis to such an extent that the symptoms of multiple sclerosis will not be manifested. Further, the drug's adverse effects on an already weakened immune system can be minimized if the imidazole used for treatment of multiple sclerosis is metronidazole.

It is foreseen that a maintained dosage of the imidazole will be required virtually for the life of the treated patient to prevent the multiple sclerosis virus from again becoming active and causing reoccurring symptoms.

It is theorized that almost any virus may be controlled to some extent with the imidazole compounds of the present invention. It is thus foreseen that the treatment disclosed herein may be effective for diseases theorized to be virally induced, including: autosomal dominant genetic disease, polycystic renal disease, insulin dependent diabetes mellitus, hereditary breast cancer, Huntington's disease, Duchenne muscular dystrophies, and auto-immune deficiency syndrome (AIDS). In particular, it is contended that multiple sclerosis may be effectively treated with imidazoles and derivatives thereof.

While administration of a large initial concentration of the therapeutic agent followed by a tapering off of concentration throughout the day has been found to be highly effective in treating the virus, certain of the imidazoles cause some peripheral nerve damage, as identified by tingling of the skin or the like. Applicant has found that a single daily or less frequent large dose of the agent rather than multiple small doses are less likely to result in such nerve damage, especially when the imidazole is metronidazole.

As noted above, it is theorized that the imidazole moeity acts by suppressing viral production while natural body defenses function to eliminate the virus from the system. It is also theorized that the effectiveness of the imidazole derivatives relates to their ability to block or interfere with the viral metabolism cycle. However, many years of careful experimentation will be necessary to prove or disprove these theories and it is not the intent of the applicant to be confined to them for purposes of this application.

DETAILED DESCRIPTION AND EXAMPLES

As required, detailed embodiments of the present invention are disclosed herein; however, it is to be understood that the disclosed embodiments are merely exemplary of the invention which may be embodied in various forms. Therefore, specific details disclosed herein are not to be interpreted as limiting, but merely as a basis for the claims and as a representative basis for teaching one skilled in the art to variously employ the present invention in virtually any appropriately detailed structure.

Imidazole derivatives of sufficient bioavailability are theorized to be effective antiviral agents. Bioavailability refers to the ability of the drug to move through the involved biological system to the active site at which it can act upon the virus.

Of course, practical application of these imidazole drugs requires that the moeity, or substituted moeity, be part of a pharmaceutically acceptable compound. That is, the compound must not exhibit significant toxic effects at its therapeutic levels and it should not be appreciably carcinogenic. Therefore, the only significant limitations on drugs having the substituted imidazole moeity for use according to the present invention are pharmaceutical acceptability and bioavailability. Cimetidine is a drug that includes the imidazole moeity, has the appropriate bioavailability and is sufficiently low in toxicity to be effective as an antiviral agent. Specific examples and hypotheticals describing treatment with these drugs, or their acid salts, of multiple sclerosis are presented below.

The preferred treatment process involves administration of the anti-viral agent in large relatively infrequent dosages, once a day or less frequently with metronidazole and other imidazoles having relatively long half lives within the patient. With cimetidine and other imidazoles having relatively short half lives, more frequent doses are necessary; for example, two doses per day for cimetidine. The dosage depends on body weight and the imidazole utilized. For cimetidine, doses of 1200 to 2000 milligrams per day as tolerated in patients given on a frequency of twice per day have been effective. During treatment for active symptoms, the dosage may be greater than for maintenance once the active symptoms caused by the virus have stopped. A large dose once a day or the like will permit the inducement of a high concentration of the agent in the biological system for a short period of time followed by a tapering off of the concentration. This should lead to effective treatment while at the same time avoiding toxicity problems and side effects.

While the above described treatment has been directed to humans having multiple sclerosis, it is foreseen that the treatment method may be applicable to a wide variety of virally induced or enhanced diseases.

It is to be understood that while certain forms of the present invention have been illustrated and described herein, it is not to be limited to the specific forms or arrangement of parts described and shown.

What is claimed and desired to be secured by Letters Patent is as follows:

1. A method for treating a human host having multiple sclerosis comprising repeatedly orally administering a composition including cimetidine to a human host in need of said treatment, said administration including a dose having cimetidine in a range from approximately 30 mg to 2500 mg on an average per 24 hour period.

2. The method of claim 1 wherein said dosage is substantially reduced following initial administration over a period including a plurality of months.

3. A method according to claim 1 wherein said dosage includes about 30 milligrams of cimetidine per kilogram body weight per day.

4. A method according to claim 1 wherein said dosage is given in an effective single oral administration of approximately 30 milligrams of cimetidine per kilogram body weight every 12 hours.

5. A method according to claim 1 wherein said dosage is given at intervals of greater than once every twenty-four hours.

6. A method for treating a human host having multiple sclerosis comprising repeatedly orally administering to said host effective anti-viral amounts of a pharmaceutically acceptable composition comprising an imidazole selected from the group consisting of cimetidine and pharmaceutically acceptable salts thereof and having sufficient bioavailability to be transported to the situs of the viral infection.

* * * * *